(12) United States Patent
Hariri

(10) Patent No.: US 10,113,146 B2
(45) Date of Patent: *Oct. 30, 2018

(54) METHOD OF COLLECTING PLACENTAL STEM CELLS

(71) Applicant: Celularity, Inc., Warren, NJ (US)

(72) Inventor: Robert J. Hariri, Bernardsville, NJ (US)

(73) Assignee: CELULARITY, INC., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/177,779

(22) Filed: Jun. 9, 2016

(65) Prior Publication Data

US 2016/0289634 A1 Oct. 6, 2016

Related U.S. Application Data

(60) Division of application No. 14/298,294, filed on Jun. 6, 2014, now Pat. No. 9,387,283, which is a division of application No. 12/618,664, filed on Nov. 13, 2009, now Pat. No. 8,986,984, which is a continuation of application No. 11/187,400, filed on Jul. 21, 2005, now Pat. No. 7,638,141, which is a continuation of application No. 10/004,942, filed on Dec. 5, 2001, now Pat. No. 7,045,148.

(60) Provisional application No. 60/251,900, filed on Dec. 6, 2000.

(51) Int. Cl.
| | |
|---|---|
| A01N 1/02 | (2006.01) |
| A01N 63/02 | (2006.01) |
| C12N 5/073 | (2010.01) |
| A61M 1/02 | (2006.01) |
| C12N 5/0775 | (2010.01) |
| A61K 35/50 | (2015.01) |
| C12M 1/00 | (2006.01) |
| C12N 5/0789 | (2010.01) |
| A61K 35/12 | (2015.01) |
| A61K 48/00 | (2006.01) |

(52) U.S. Cl.
CPC ........... *C12N 5/0605* (2013.01); *A01N 1/021* (2013.01); *A61K 35/50* (2013.01); *A61M 1/02* (2013.01); *C12M 29/10* (2013.01); *C12M 47/04* (2013.01); *C12N 5/0603* (2013.01); *C12N 5/0647* (2013.01); *C12N 5/0668* (2013.01); *A61K 35/12* (2013.01); *A61K 48/00* (2013.01); *A61K 2035/124* (2013.01); *A61M 2202/0462* (2013.01); *A61M 2210/1458* (2013.01); *A61M 2210/1466* (2013.01); *C12N 2509/00* (2013.01); *C12N 2510/02* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 7,045,148 B2* | 5/2006 | Hariri | ...................... | A61M 1/02 424/529 |
| 7,255,879 B2* | 8/2007 | Hariri | ...................... | A61M 1/02 424/529 |
| 8,986,984 B2* | 3/2015 | Hariri | .................... | A01N 1/021 435/1.2 |
| 9,387,283 B2* | 7/2016 | Hariri | .................... | A01N 1/021 |

* cited by examiner

*Primary Examiner* — Qian Janice Li
(74) *Attorney, Agent, or Firm* — Celularity, Inc.; Timothy L. Smith; Geoffrey T. Knudsen

(57) ABSTRACT

A method of collecting embryonic-like stem cells from a placenta which has been treated to remove residual cord blood by perfusing the drained placenta with an anticoagulant solution to flush out residual cells, collecting the residual cells and perfusion liquid from the drained placenta, and separating the embryonic-like cells from the residual cells and perfusion liquid. Exogenous cells can be propagated in the placental bioreactor and bioactive molecules collected therefrom.

24 Claims, 8 Drawing Sheets

METHOD OF COLLECTING PLACENTAL STEM CELLS

BENEFIT OF PRIOR PROVISIONAL APPLICATION

This application is a divisional of U.S. patent application Ser. No. 14/298,294, filed Jun. 6, 2014, which is a divisional of U.S. application Ser. No. 12/618,664, filed Nov. 13, 2009 (now U.S. Pat. No. 8,986,984), which is a continuation of U.S. application Ser. No. 11/187,400 (now U.S. Pat. No. 7,638,141), filed Jul. 21, 2005, which is a continuation of U.S. application Ser. No. 10/004,942 (now U.S. Pat. No. 7,045,148), filed Dec. 5, 2001, which claims benefit of U.S. Provisional Application Ser. No. 60/251,900, filed Dec. 6, 2000, the specifications of which are each incorporated herein by reference.

BACKGROUND OF THE INVENTION

1. Field of the Invention

The present invention is generally in the area of stem cell collection, and particularly in the recovery of embryonic-like stem cells and other multipotent stem cells from placentas. These embryonic-like stem cells are derived from the placenta collected after birth. These embryonic-like stem cells have characteristics of embryonic stem cells but are not derived from the embryo.

2. Description of the Background Art

Human stem cells are totipotential or pluripotential precursor cells capable of generating a variety of mature human cell lineages. This ability serves as the basis for the cellular differentiation and specialization necessary for organ and tissue development. Recent success at transplanting such stem cells have provided new clinical tools to reconstitute and/or supplement the bone marrow after myeloablation due to disease, exposure to toxic chemical or radiation. Further evidence exists which demonstrates that stem cells can be employed to repopulate many, if not all, tissues and restore physiologic and anatomic functionality. The application of stem cells in tissue engineering, gene therapy delivery and cell therapeutics is also advancing rapidly.

Obtaining sufficient human stem cells has been problematic for several reasons. First, isolation of normally occurring populations of stem cells in adult tissues has been technically difficult, costly and very limited in quantity. Secondly, procurement of these cells from embryos or fetal tissue including abortuses has raised many ethical and moral concerns. The widely held belief that the human embryo and fetus constitute independent life has justified a moratorium on the use of such sources for any purpose. Alternative sources which do not violate the sanctity of independent life would be essential for further progress in the use of stem cells clinically.

Umbilical cord blood (cord blood) is a known source of hemopoietic pluripotent, progenitor stem cells that are cryopreserved for use in hemopoietic reconstitution. The use of cord blood for this purpose is well known and is becoming a widely used therapeutic procedure. The conventional technique for the collection of cord blood is based on the use of a needle or cannula which is used with the aid of gravity to drain the cord blood from the placenta. Usually the needle or cannula is placed in the umbilical vein and the placenta is gently massaged to aid in draining the cord blood from the placenta. Thereafter the drained placenta has been considered to be of no use and has typically been discarded. A major limitation of stem cell procurement from cord blood has been the frequently inadequate volume of cord blood obtained resulting in insufficient cell numbers to reconstitute bone marrow after transplantation.

Stem cells are in critically short supply. These are important for the treatment of a wide variety of disorders, including malignancies, inborn errors of metabolism, hemoglobinopathies, and immunodeficiencies. It would be highly advantageous to have a source of more embryonic stem cells.

Accordingly, it is a primary object of the present invention to provide a method of extracting and recovering hematopoietic stem cells from an exsanguinated placenta.

It is also an object of the invention to provide a method for isolating other embryonic-like and/or omnipotent stem cells from an extractant of a drained placenta.

It is a further object of the invention to provide a method to collect stem cells from the umbilical cord vein, the best source of hemopoietic pluripotent progenitor stem cells.

It is a further object of the present invention to provide a method and means whereby additional embryonic-like stem cells in higher concentrations can be obtained from a drained placenta.

It is a further object of the invention to provide a method of utilizing the isolated and perfused placenta as a bioreactor providing a good environment for the propagation of endogenous cells, including but not limited to lymphocytes and stem cells.

It is a further object of the present invention to provide a method and means whereby stem cells can be obtained many hours following the birth and expulsion of the placenta from the uterus.

SUMMARY OF THE INVENTION

A method of extracting embryonic-like stem cells from a drained placenta by means of a perfusion technique which utilizes either or both of the umbilical artery and umbilical vein has been developed, on the recovery of human placenta following exsanguination and collection of the residual blood. The placenta is then processed in such a manner as to establish an ex vivo, natural bioreactor environment in which resident stem cells within the parenchyma and extravascular space are recruited and migrate into the empty microcirculation where they can be washed into a collecting vessel by perfusion.

DETAILED DESCRIPTION OF THE INVENTION

I. Method of Draining and Extracting Placenta

Draining of Cord Blood and Storage of Fresh Placenta

The method requires access to freshly drained human placentas which have been subjected to a conventional cord blood recovery process by draining substantially all of the cord blood from the placenta. It is important that the placenta be properly stored and drained if it is to be a suitable source of embryonic stem cells. Generally, a placenta should be stored in an anticoagulant solution at a temperature of 5 to 25° C. (centigrade) for no more than 48 hours prior to the collection of the cord blood. Suitable anticoagulant solutions are well known. A preferred anticoagulant solution comprises a solution of heparin (1% w/w in 1:1000 solution). Generally, the drained placenta should be stored for no more than 36 hours before the embryonic-like stem cells are collected.

Extraction of Cells

The preferred embryonic-like stem cell extraction method is based on the perfusion of the drained placenta with a suitable aqueous fluid such as an anticoagulant dissolved in any suitable aqueous isotonic fluid such as 0.9N sodium chloride solution. The anticoagulant for the perfusion liquid may comprise heparin or warfarin sodium at a concentration which is sufficient to prevent the formation of clots of any residual cord blood. Generally from 100 to 1000 units of heparin may be employed.

Figure 1:
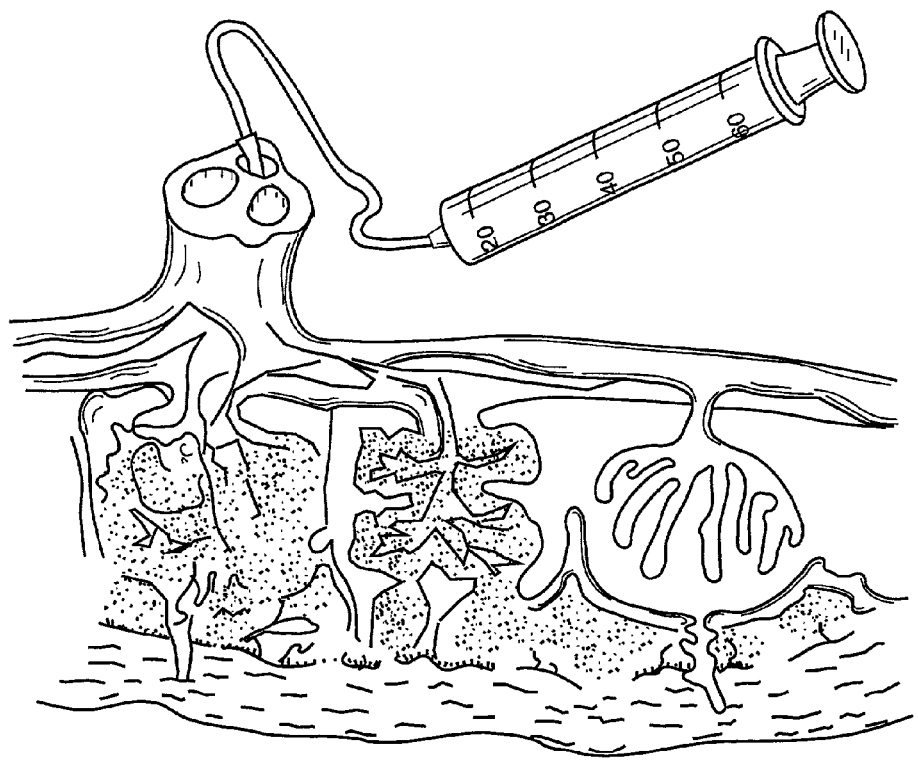
FIG. 1 is a cross-sectional view of the cannulation of the vein and artery of a placenta to perfuse the placenta and then collect the perfusate.
Figure 2A:
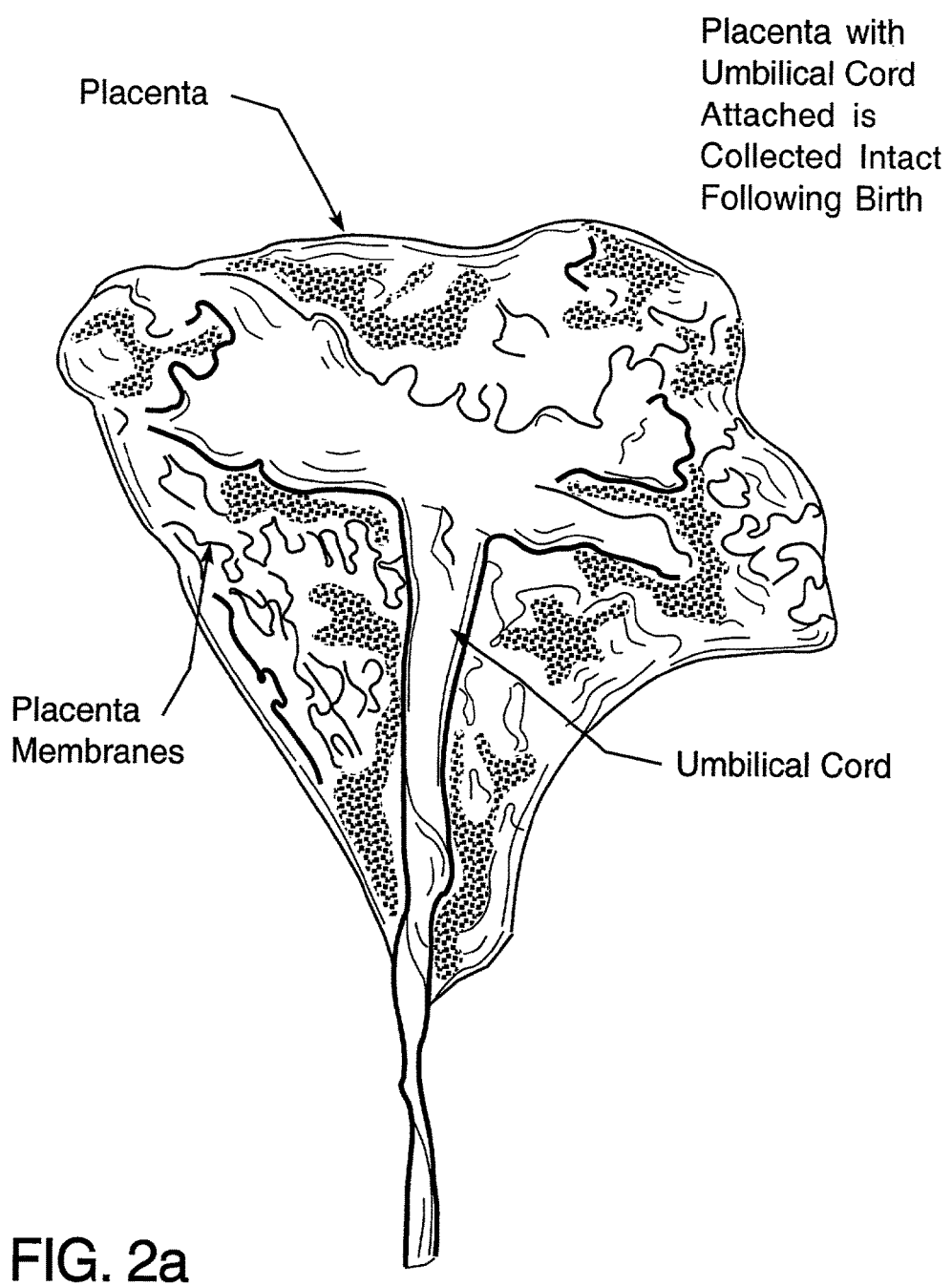
FIGS. 2a-e are schematics showing the collection, clamping, perfusion, collection and storage of a drained and perfused placenta.
Figure 2B:
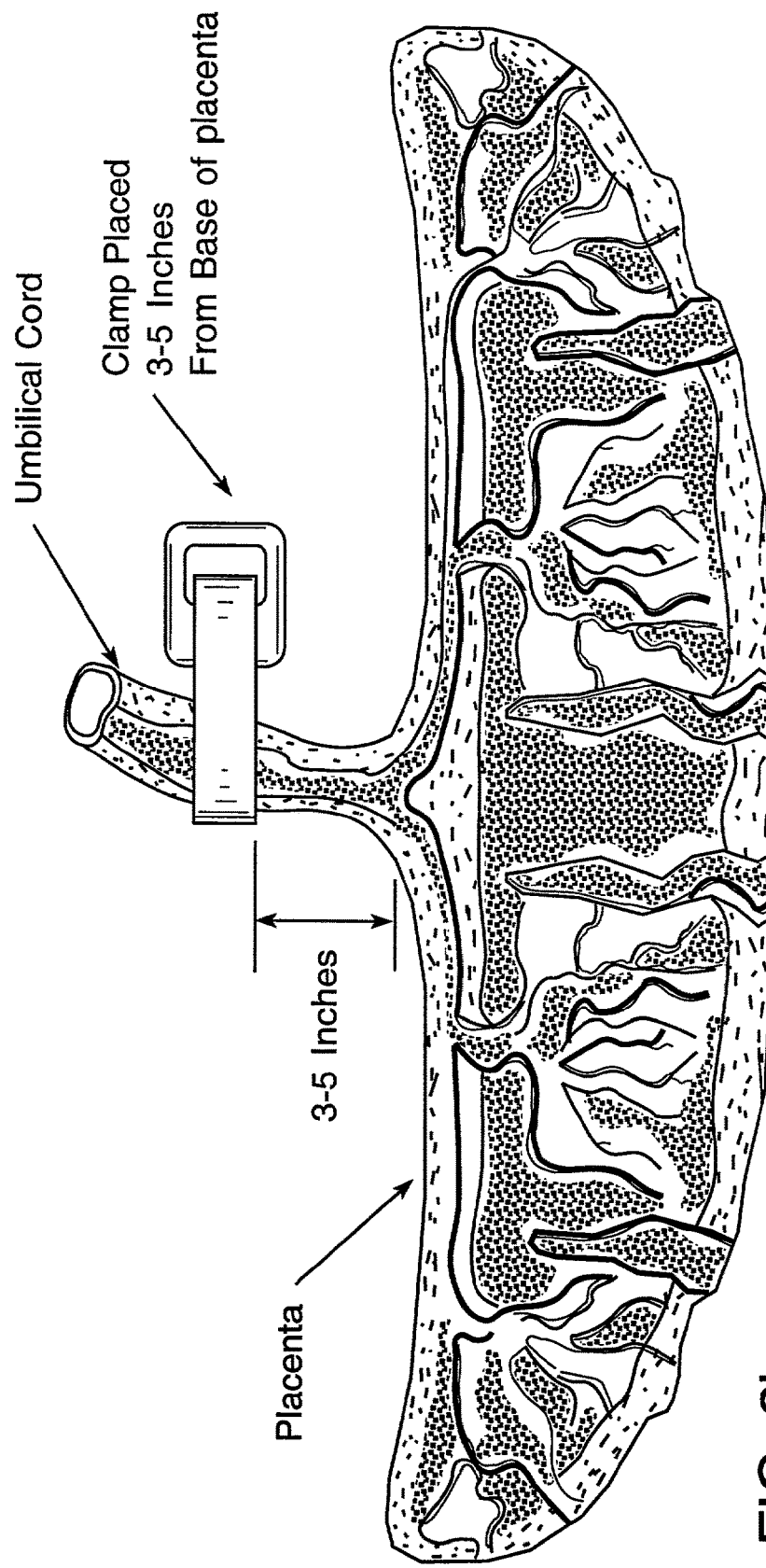
Figure 2C:
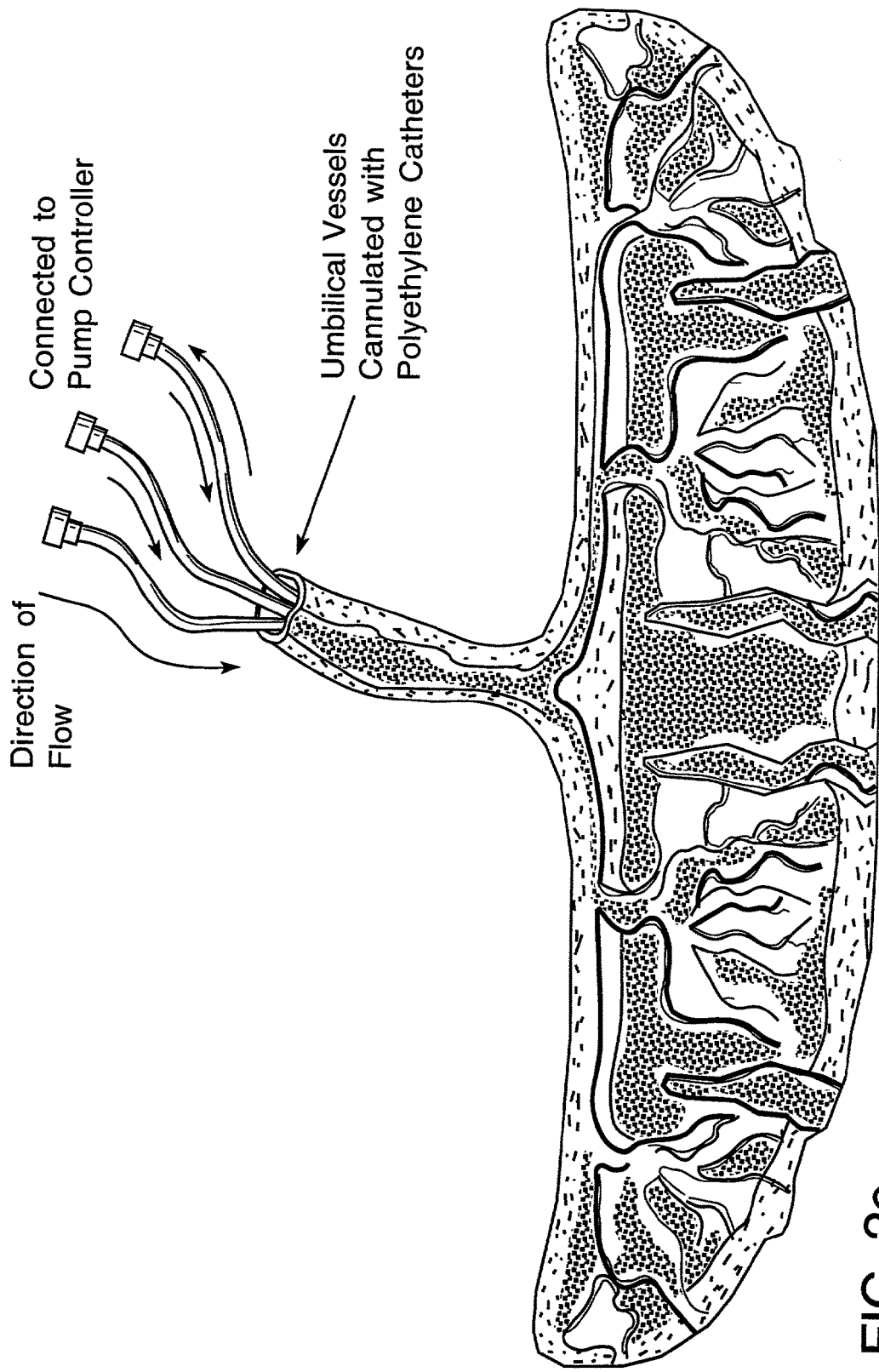
Figure 2D:
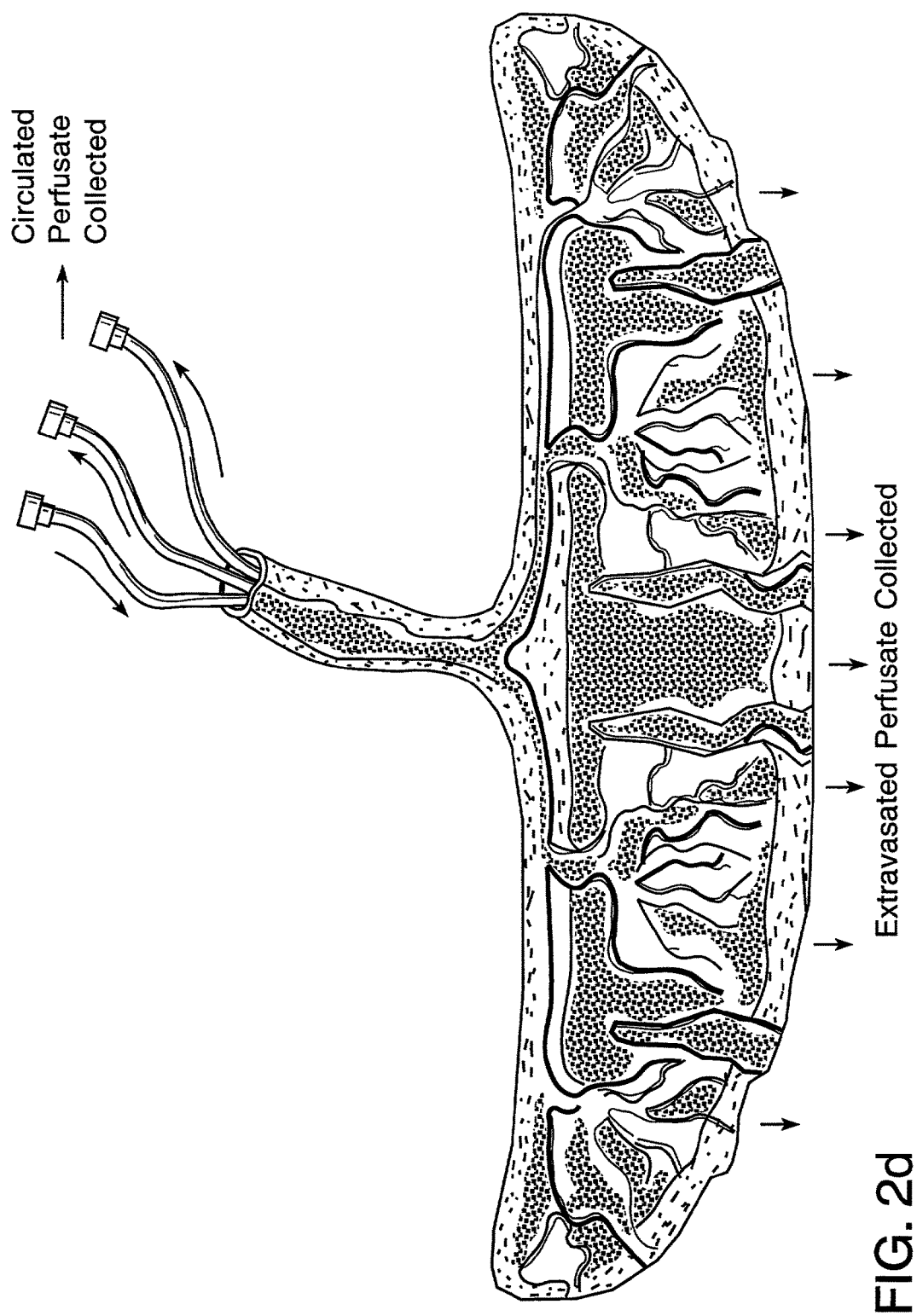
Figure 2E:
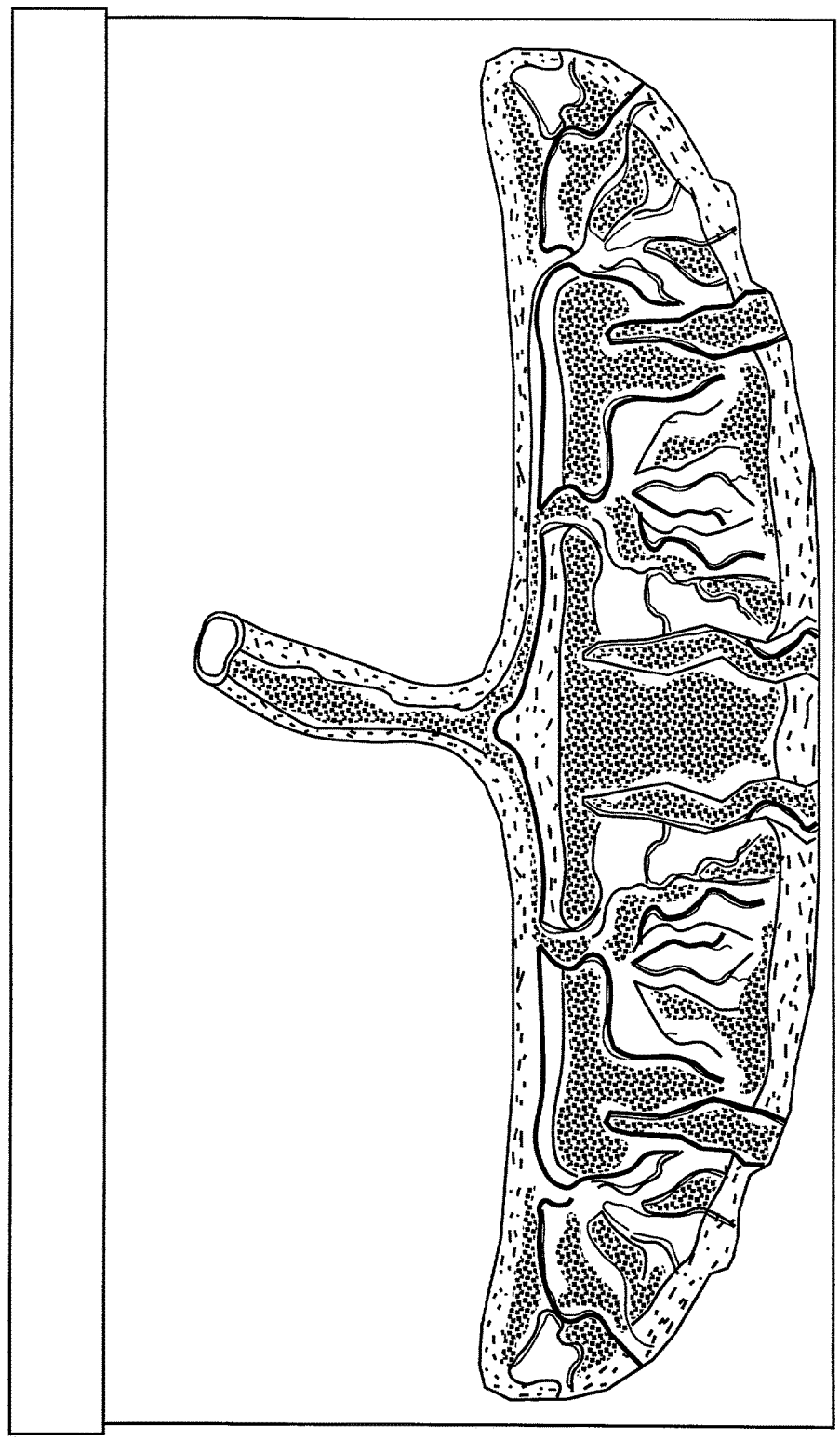

The extraction procedure is based on the passage of the perfusion liquid through either or both of the umbilical artery and umbilical vein using a gravity flow into the placenta which is suspended in such a manner that the umbilical artery and umbilical vein are at the highest point. It is preferred to connect the umbilical artery and the umbilical vein simultaneously as shown in FIG. 1 to a pipette that is connected via a flexible connector to a reservoir of the perfusion liquid which is passed into the umbilical vein and artery and collected in a suitable open vessel from the surface of the placenta that was attached to the uterus of the mother during gestation.

The collection technique is based on the use of a sufficient amount of the perfusion liquid that will result in the collection of the cells left after the drainage of the cord blood. It has been observed that when the perfusion liquid is first collected, the liquid is colored with the residual red blood cells and tends to become clear as the perfusion liquid is passed through the placenta. Generally from 30 to 100 ml of perfusion liquid is adequate to collect the embryonic-like cells but more or less may be used depending on the observed results.

II. Method of Using the Drained and Perfused Placenta as a BioReactor

Perfusion of the Drained Placenta

As discussed above, the placenta is recovered under aseptic conditions following exsanguination and clamping of the proximal umbilical cord (within 4-5 cm (centimeter) of the insertion into the placental disc) and placental blood recovery and transported in a sterile, thermally insulated (maintaining the temperature of the placenta between 20-28° C.) transport device to the laboratory for processing, for example, by placing the clamped placenta in a sterile ziplock plastic bag which is then placed in an insulated Styrofoam container or vacuum insulation container, as shown in FIGS. 2*a-e*.

Use of the Placenta as a Bioreactor

Figure 3:
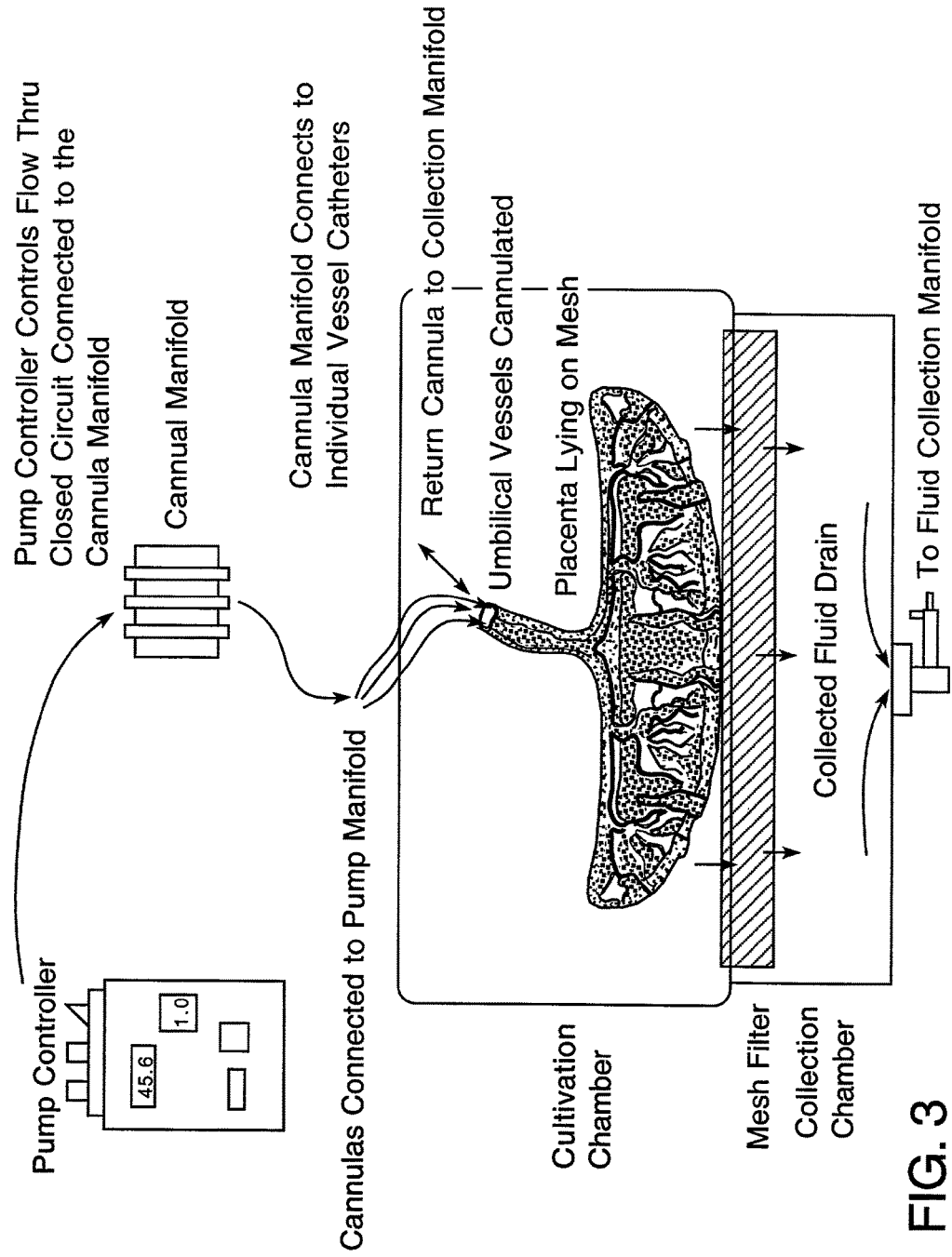
FIG. 3 is a cross-sectional schematic of a perfused placenta in a device for use as a bioreactor.

The placenta is placed in a sterile basin and washed with 500 mL of phosphate-buffered normal saline. The wash fluid is discarded. The umbilical vein is cannulated with a Teflon or plastic cannula connected to sterile tubing which is connected to the perfusion manifold, as shown in FIG. 3. The basin is then covered and the placenta is maintained at room temperature (20-25° C.) for a period varying from 2 to 24 hours. The placenta is then perfused at periodically, preferably at 4, 8, 12, and 24 hours, with a volume of perfusate, preferably 100 mL of perfusate (sterile normal saline supplemented with or without 1000 u/L heparin and/or EDTA and/or CPDA (creatine phosphate dextrose)). The effluent fluid which escapes the placenta at the opposite surface is collected and processed to isolate the stem cells of interest. Alterations in the conditions in which the placenta is maintained and the nature of the perfusate can be made to modulate the volume and composition of the effluent.

Figure 4:
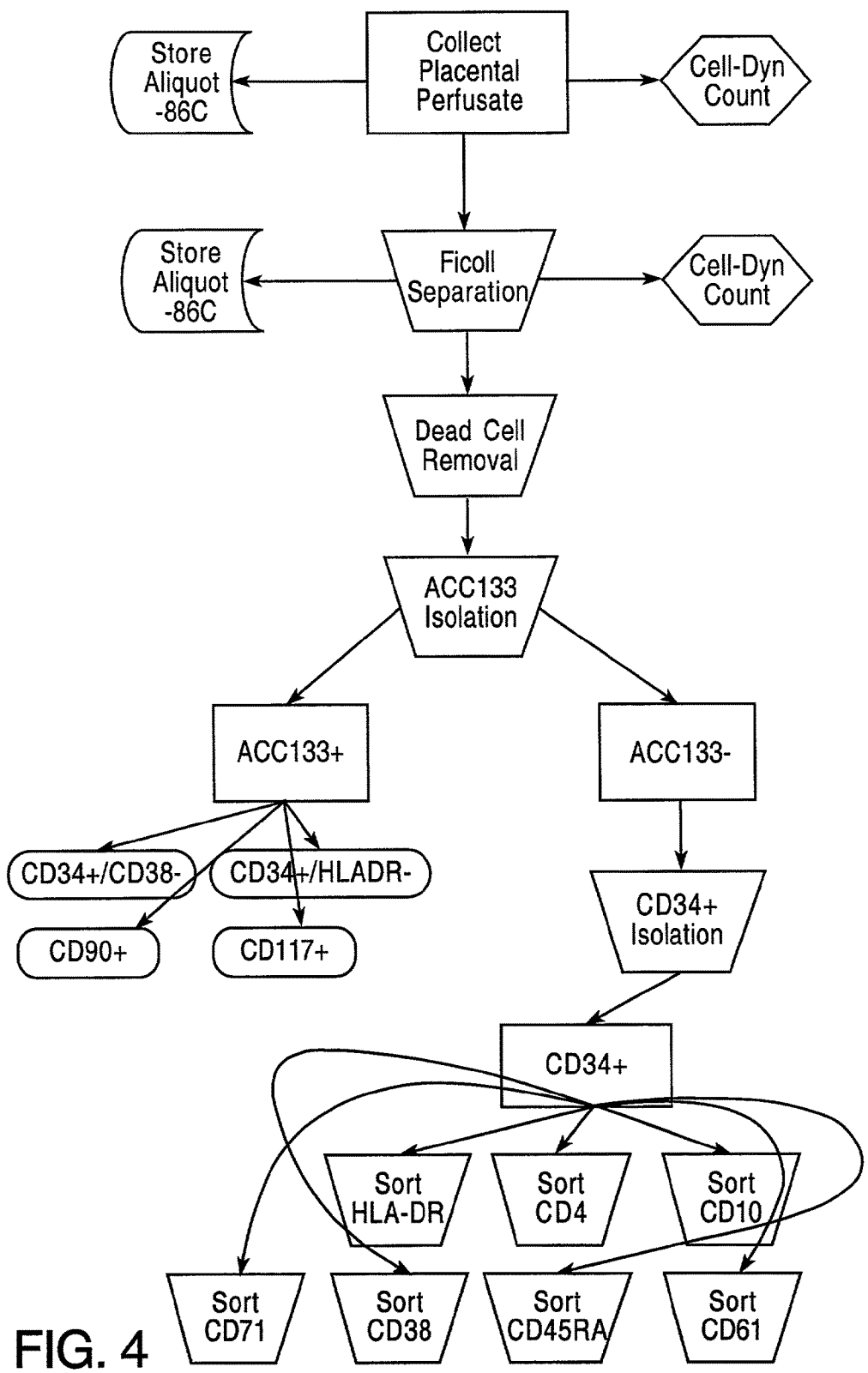
FIG. 4 is a selection scheme for sorting cells retrieved from a perfused placenta.

Stem cells are then isolated from the effluent using techniques known by those skilled in the art, such as for example, density gradient centrifugation, magnet cell separation or other acceptable method, and sorted, for example, according to the scheme shown in FIG. 4.

In variations of this method, the cells in the placenta can be stimulated to produce bioactive molecules, such as immunoglobulin, or other molecules, or stimulated to proliferate, for example, by administration of erythropoietin. The cells can also be genetically engineered prior to harvest, while still in the bioreactor, or at the time of harvest, using for example a viral vector such as an adenoviral or retroviral vector, or using mechanical means such as liposomal or chemical mediated uptake of the DNA.

The procedure is as follows:
1. Fully exsanguinate the placenta and remove any adherent coagulated and non-adherent cellular contaminants.
2. Cultivate and perfuse the placenta with perfusate solution (for example, normal saline solution) with or without an anticoagulant, and/or with or without an antimicrobial agent.
3. Collect both the extravasated perfusate and circulated perfusate into a sterile receptacle.
4. Isolate cell types from the collected perfusate by employing techniques known by those skilled in the art, such as for example, but not limited to density gradient centrifugation, magnet cell separation, affinity cell separation or differential adhesion techniques.

In one embodiment of the invention, the placenta is used as a bioreactor for endogenous cells, including but not limited to lymphocytes and various kinds of pluripotent and/or totipotent stem cells, by incubating the placenta for 48 hours with perfusate solution.

In another embodiment the placenta is processed to remove all endogenous cells and allowing foreign cells to be introduced and propagated in the environment of the perfused placenta. In a particular embodiment the perfused placenta is irradiated with electromagnetic, UV, X-ray, gamma- or beta-radiation to eradicate all remaining viable endogenous cells. The foreign cells of interest to be propagated in the irradiated placental bioreactor are then introduced.

The exogenous cells are induced to propagate by introduction of nutrients and growth factors into the perfusion solution. Serum and other growth factors are added to the propagation perfusion solution or medium. Growth factors are usually proteins and include but are not limited to cytokines, lymphokines, interferons, colony stimulating factors (CSF's), interferons, chemokines, and interleukins. Other growth factors include recombinant human hemopoietic growth factors including ligands, stem cell factors, thrombopoeitin (Tpo), interleukins, and granulocyte colony-stimulating factor (G-CSF). The growth factors introduced into the perfusion solution can stimulate the propagation of undifferentiated stems cells or differentiated hemopoietic cells and stimulate the production of bioactive molecules including but not limited to immunoglobulins, hormones, or other growth factors as previously described.

The present invention will be further understood by reference to the following example.

Example 1: Perfusion of Drained Placenta

Twenty ml (milliliter) of phosphate buffered saline solution (PBS) is added to the perfusion liquid and a 10 ml portion is collected and centrifuged for 25 minutes at 3000 rpm (revolutions per minute). The effluent is divided into four tubes and placed in an ice bath. 2.5 ml of a 1% fetal calf serum (FCS) solution in PBS is added and the tubes are centrifuged (140 minutes×10 g (acceleration due to gravity)). The pellet is resuspended in 5 ml of 1% FCS and two tubes are combined. The total mononucleocytes are calculated by adding the total lymphocytes and the total monocytes and multiplying this by the total cell suspension volume.

Example 2: Analysis of Cells Obtained by Perfusion and Incubation of Placenta

|  | WBC 1000/ml | Lym % | MID % | GRA % | Total Volume | # of Cells |
|---|---|---|---|---|---|---|
| CB (Cord Blood) | 10.5 | 43.2 | 8 | 48.8 | 60 ml | $6.3 \times 10^8$ |
| PP (Placenta perfusate, room temperature) | 12.0 | 62.9 | 18.2 | 18.9 | 15 ml | $1.8 \times 10^8$ |
| $PP_2$ (Placenta perfusate, 37° C.) | 11.7 | 56.0 | 19.2 | 24.8 | 30 ml | $3.5 \times 10^8$ |

Samples of PP were after Ficoll.
Total cell number of PP after Ficoll is $5.3 \times 10^8$ and number of CB before processing is $6.3 \times 10^8$. Lym % is percent of lymphocytes; MID % is percent of midrange white blood cells; and GRA % is percent of granulocytes.
Cell isolation is achieved by using magnetic cell separation, such as for example, Auto Macs (Miltenyi). Preferably, $CD\ 34^+$ cell isolation is performed first.

Materials and Methods

Placenta donors were recruited from expectant mothers that enrolled in private umbilical cord blood banking programs and provided informed consent permitting the use of the exsanguinated placenta following recovery of cord blood for research purposes. These donors also permitted use of blinded data generated from the normal processing of their umbilical cord blood specimens for cryopreservation. This allowed comparison between the composition of the collected cord blood and the effluent perfusate recovered using this experimental method described below. All donor data is confidential.

Following exsanguination of the umbilical cord and placenta, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23+/−2° C.) or refrigerated (4° C.) in sterile containers for 2 to 20 hours. Periodically, the placentas were immersed and washed in sterile saline at 25+/−3° C. to remove any visible surface blood or debris. The umbilical cod was transected approximately 5 cm from its insertion into the placenta and the umbilical vessels were cannulated with Teflon or polypropylene catheters connected to a sterile fluid path allowing bi-directional perfusion of the placenta and recovery of the effluent fluid. The system employed in the present invention enabled all aspects of conditioning, perfusion and effluent collection to be performed under controlled ambient atmospheric conditions as well as real-time monitoring of intravascular pressure and flow rates, core and perfusate temperatures and recovered effluent volumes. A range of conditioning protocols were evaluated over a 24 hour post-partum period and the cellular composition of the effluent fluid was analyzed by flow cytometry, light microscopy and colony forming unit assays.

Placental Conditioning

The placenta was maintained under varying conditions in an attempt to simulate and sustain a physiologically compatible environment for the proliferation and recruitment of residual cells. The cannula was flushed with IMDM serum-free medium (GibcoBRL, NY) containing 2 U/ml heparin (Elkins-Sinn, NJ). Perfusion of the placenta continued at a rate of 50 mL per minute until approximately 150 mL of perfusate was collected. This volume of perfusate was labeled "early fraction". Continued perfusion of the placenta at the same rate resulted in the collection of a second fraction of approximately 150 mL and was labeled "late fraction". During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were obtained from delivery rooms along with cord blood after obtaining written parental consent, and were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection. Placentas were then perfused with heparinized (2 U/mL) Dulbecco's modified Eagle Medium (H.DMEM) at the rate of 15 mL/minute for 10 minutes and the perfusates were collected from the maternal sites within one hour and the nucleated cells counted. The perfusion and collection procedures were repeated once or twice until the number of recovered nucleated cells fell below 100/microL. The perfusates were pooled and subjected to light centrifugation to remove platelets, debris and de-nucleated cell membranes. The nucleated cells were then isolated by Ficoll-Hypaque density gradient contrifugation and after washing, resuspended in H.DMEM. For isolation of the adherent cells, aliquots of $5-10 \times 10^6$ cells were placed in each of several T-75 flasks and cultured with commercially available Mesenchymal Stem Cell Growth Medium (MSCGM) obtained from BioWhittaker, and placed in a tissue culture incubator (37° C., 5% $CO_2$). After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

Cell Recovery and Isolation

Cells are recovered from the perfusates by centrifugation at X 00×g for 15 minutes at room temperature. This procedure served to separate cells from contaminating debris and platelets. The cell pellets were resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer.

Viability was evaluated by trypan blue exclusion. Isolation of mesenchymal cells was achieved by "differential trypsinization," using a solution of 0.05% trypsin with 0.2% EDTA (Sigma). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization, using Trypsin Neutralyzing Solution (TNS, BioWhitaker). The cells were washed in H.DMEM and resuspended in MSCGM. Flow cytometry was carried out using a Becton-Dickinson FACSCalibur instrument and FITC and PE labeled monoclonal antibodies, selected on the basis of known markers for bone marrow-derived MSC (mesenchymal stem cells), were purchased from B.D. and Caltag laboratories (S.San Francisco, Calif.), and SH2, SH3 and Sh4 antibody producing hybridomas were obtained from AM. Cul. and reactivities of the MoAbs in their cultured supernatants were detected by FITC or PE labeled F(ab)'2 goat anti-mouse antibodies. Lineage differentiation was carried out using the commercially available induction and maintenance culture media (BioWhittaker), used as per manufacturer's instructions.

Isolation of Placental Stem Cells

Microscopic examination of the adherent cells in the culture flasks revealed morphologically different cell types. The spindle-shaped cells, the round cells with large nuclei and numerous peri-nuclear small vacuoles and star-shaped cells with several projections, through one of which the cells were attached to the flask. Although no attempts were made to further characterize these adherent cells, similar cells were observed in the culture of bone marrow, cord and peripheral blood, and therefore considered to be non-stem cell in nature. The fibroblastoid cells, appearing last as clusters, were candidates for being MSC and were isolated by differential trypsinization and subcultured in secondary flasks. Phase microscopy of the rounded cells, after trypsinization, to be highly granulated; indistinguishable from the bone marrow-derived MSC produced in the laboratory or purchased from BioWhittaker. When subcultured, the placental-derived cells, in contrast to their earlier phase, adhered within hours, assumed characteristic fibroblastoid shape, and formed a growth pattern identical to the reference bone marrow-derived MSC. Moreover, during subculturing and refeeding, the loosely bound mononuclear cells were washed out and the cultures remained homogeneous and devoid of any visible non-fibroblastoid cell contaminants.

Flow Cytometry

The expression of CD-34, CD-38, and other stem cell-associated surface markers on early and late fraction purified mononuclear cells was assessed by flow cytometry. Briefly, cells were washed in PBS and then double-stained with anti-CD34 phycoerythrin and anti-CD38 fluorescein isothiocyanate (Becton Dickinson, Mountain View, Calif.).

Whereas particular embodiments of this invention have been described herein for purposes of illustration, it will be evident to those persons skilled in the art that numerous variations of the details of the present invention may be made without departing from the invention as defined in the appended claims.

What is claimed is:

1. A method of collecting embryonic-like stem cells from a placenta which has been treated to remove residual cord blood said method comprising:
    perfusing a placenta which has been drained of cord blood with an anticoagulant perfusion solution to flush out residual cells and embryonic-like stem cells from said drained placenta, and
    collecting said residual cells and embryonic-like stem cells and perfusion solution from the drained placenta.

2. The method of claim 1 further comprising separating said embryonic-like stem cells from said residual cells and anticoagulant perfusion solution.

3. The method of claim 1 wherein the placenta is perfused with the anticoagulant solution by passing the anticoagulant solution into one or both of the umbilical artery and umbilical vein of said placenta.

4. The method of claim 1 including collecting said residual cells and said anticoagulant perfusion solution from the part of the placenta that was attached to the wall of the uterus of the mother.

5. The method of claim 2 including said embryonic-like stem cells are separated from said residual cells and anti-coagulant perfusion solution by centrifugation.

6. The method of claim 1 including
    continuing perfusion of said placenta for maintaining placental viability,
    flushing out additional residual cells and additional embryonic-like stem cells,
    collecting said additional residual cells, said additional embryonic-like stem cells and said additional anticoagulant perfusion solution, and
    separating said additional embryonic-like stem cells from said additional residual cells.

7. The method of claim 6 including maintaining said perfusion of said placenta for stimulating the production of new cells and bioactive molecules, and collecting said newly produced cells and said bioactive molecules from said placenta.

8. The method of claim 6 wherein the residual cells and embryonic-like stem cells are collected over a period of 24 to 48 hours after birth.

9. The method of claim 6 wherein the placenta or cells in the placenta are stimulated to produce bioactive molecules.

10. The method of claim 7 wherein said newly produced cells and bioactive molecules are collected over a period of 24 to 48 hours after birth.

11. The method of claim 6 wherein the cells in the placenta are genetically engineered with exogenous DNA.

12. The method of claim 7 wherein the newly produced cells are genetically engineered with exogenous DNA.

13. A method of propagating exogenous cells in a placental bioreactor which has been treated to remove residual umbilical cord blood, comprising:
    perfusing a placenta which has been drained of cord blood with an anticoagulant perfusion solution to flush out residual cells and embryonic-like stem cells,
    collecting said residual cells, said embryonic-like stem cells, and said anticoagulant perfusion solution from the drained placenta,
    removing all remaining viable endogenous cells from the drained placenta,
    perfusing the placenta with nutrient perfusion solution,
    introducing exogenous cells into the perfused placenta,
    incubating the perfused placenta with exogenous cells, and
    collecting propagated exogenous cells from the perfused placenta.

14. The method of claim 13 wherein the remaining viable endogenous cells are removed by irradiation of the perfused placenta.

15. The method of claim 14 wherein the irradiation is selected from electromagnetic, ultra-violet, X-ray, gamma-, and beta-radiation.

16. The method of claim 13 wherein the exogenous cells are stem cells.

17. The method of claim 16 wherein the stems cells are hemopoietic pluripotent stem cells.

18. The method of claim 13 wherein the exogenous cells are stimulated to produce bioactive molecules.

19. The method of claim 18 wherein the bioactive molecules are collected prior to collecting the propagated exogenous cells.

20. The method of claim 13 wherein the exogenous cells are stimulated to propagate by introducing growth factors selected from cytokines, hormones, promoters, repressors, proteins, nucleic acids, viruses, and immunogens.

21. The method of claim 13 wherein the exogenous cells are selected from animal cells, insect cells, or human cells.

22. The method of claim 13 wherein the exogenous cells in the placenta are genetically engineered with exogenous DNA prior to collecting or during propagation in the perfused placental bioreactor.

23. The method of claim 22 wherein the exogenous DNA is introduced into the exogenous cells propagated in the perfused placenta via a vector selected from viral, adenoviral, and retroviral vectors.

24. The method of claim 22 wherein the exogenous DNA is introduced into the exogenous cells by a method selected from mechanical introduction of the exogenous DNA, chemical mediated uptake of the exogenous DNA, and liposomal mediated uptake of the exogenous DNA.

\* \* \* \* \*